(12) United States Patent
Wingeier et al.

(10) Patent No.: US 10,188,862 B2
(45) Date of Patent: *Jan. 29, 2019

(54) METHODS AND SYSTEMS FOR CONTROLLING A STATE OF A NEUROSTIMULATOR

(71) Applicant: NeuroPace, Inc., Mountain View, CA (US)

(72) Inventors: Brett Wingeier, San Francisco, CA (US); Barbara Gibb, Foster City, CA (US); Craig Baysinger, Livermore, CA (US); Thomas Tcheng, Pleasant Hill, CA (US); Suresh Gurunathan, Palo Alto, CA (US)

(73) Assignee: NeuroPace, Inc., Mountain View, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 15/257,890

(22) Filed: Sep. 6, 2016

(65) Prior Publication Data

US 2016/0375247 A1 Dec. 29, 2016

Related U.S. Application Data

(60) Continuation of application No. 15/135,247, filed on Apr. 21, 2016, now Pat. No. 9,463,322, which is a (Continued)

(51) Int. Cl.
*A61N 1/36* (2006.01)
*A61B 5/00* (2006.01)
(Continued)

(52) U.S. Cl.
CPC ........ *A61N 1/36128* (2013.01); *A61B 5/0031* (2013.01); *A61B 5/0476* (2013.01);
(Continued)

(58) Field of Classification Search
CPC ............ A61N 1/36128; A61N 1/36142; A61N 1/3718; A61B 5/0031; A61B 5/0476;
(Continued)

(56) References Cited

U.S. PATENT DOCUMENTS 4,088,139 A 5/1978 Auerbach
4,096,865 A 6/1978 Auerbach et al.
(Continued)

*Primary Examiner* — Mark W Bockelman
(74) *Attorney, Agent, or Firm* — Loza & Loza, LLP; David S. Sarisky

(57) ABSTRACT

A method and system is described for ensuring a state of an active implantable medical device based on the presence and persistence of a magnetic field. The output of a magnetic field sensor is monitored. The active implantable medical device is maintained in a first state, for so long as the presence of a magnetic field is detected by the magnetic field sensor, until a first interval is surpassed. If the first interval is surpassed, then a determination is made as to whether a second interval has been surpassed. If it is determined that the second interval has not been surpassed, then the active implantable medical device is transitioned into a second state. If it is determined that the second interval has been surpassed, then it is ensured that the active implantable medical device is in a predetermined one of the first and second states.

15 Claims, 6 Drawing Sheets

Related U.S. Application Data division of application No. 13/631,820, filed on Sep. 28, 2012, now Pat. No. 9,345,884.

(51) Int. Cl.
*A61B 5/0476* (2006.01)
*A61N 1/37* (2006.01)

(52) U.S. Cl.
CPC .......... *A61B 5/4094* (2013.01); *A61B 5/4836* (2013.01); *A61N 1/36067* (2013.01); *A61N 1/36142* (2013.01); *A61B 2560/0242* (2013.01); *A61B 2560/0266* (2013.01); *A61N 1/3718* (2013.01)

(58) Field of Classification Search
CPC ................ A61B 5/4836; A61B 5/4094; A61B 2560/0266; A61B 2560/0242
See application file for complete search history.

(56) References Cited

U.S. PATENT DOCUMENTS

| | | |
|---|---|---|
| 4,735,204 A | 4/1988 | Sussman et al. |
| 5,292,342 A | 3/1994 | Nelson et al. |
| 5,314,453 A | 5/1994 | Jeutter |
| 5,370,666 A | 12/1994 | Lindberg et al. |
| 6,016,449 A | 1/2000 | Fischell et al. |
| 6,044,301 A | 3/2000 | Hartlaub et al. |
| 6,101,417 A | 8/2000 | Vogel et al. |
| 6,580,947 B1 | 6/2003 | Thompson |
| 6,694,184 B2 | 2/2004 | Cappa et al. |
| 6,810,285 B2 | 10/2004 | Pless et al. |
| 6,985,773 B2 | 1/2006 | Von Arx et al. |
| 7,668,596 B2 | 2/2010 | Von Arx et al. |
| 2004/0199212 A1 | 10/2004 | Fischell et al. |
| 2009/0124848 A1 | 5/2009 | Miazga |
| 2011/0238135 A1 | 9/2011 | Marnfeldt et al. |

METHODS AND SYSTEMS FOR CONTROLLING A STATE OF A NEUROSTIMULATOR

CROSS-REFERENCE TO RELATED APPLICATION(S)

This application is a continuation of U.S. application Ser. No. 15/135,247, entitled "Methods and Systems for Controlling a State of a Neurostimulator" and filed on Apr. 21, 2016, now U.S. Pat. No. 9,463,322, which is a divisional of U.S. application Ser. No. 13/631,820, entitled "Methods and Systems for Controlling a State of a Neurostimulator" and filed on Sep. 28, 2012, now U.S. Pat. No. 9,345,884, each of which is expressly incorporated by reference herein in its entirety.

FIELD

The field relates generally to active implantable medical devices, and more particularly to selecting a state of an active implantable medical device using an external component such as a magnet.

BACKGROUND

Active implantable medical devices, for example, implantable medical devices that are configured to deliver energy or another form of treatment to the body such as for patients with epilepsy or a movement disorder, often are configurable to communicate with an external component that includes a magnet. The magnet may be used by the patient and/or a patient's caregiver (including a physician) for some level of control of the active implantable medical devices.

Figure 1:
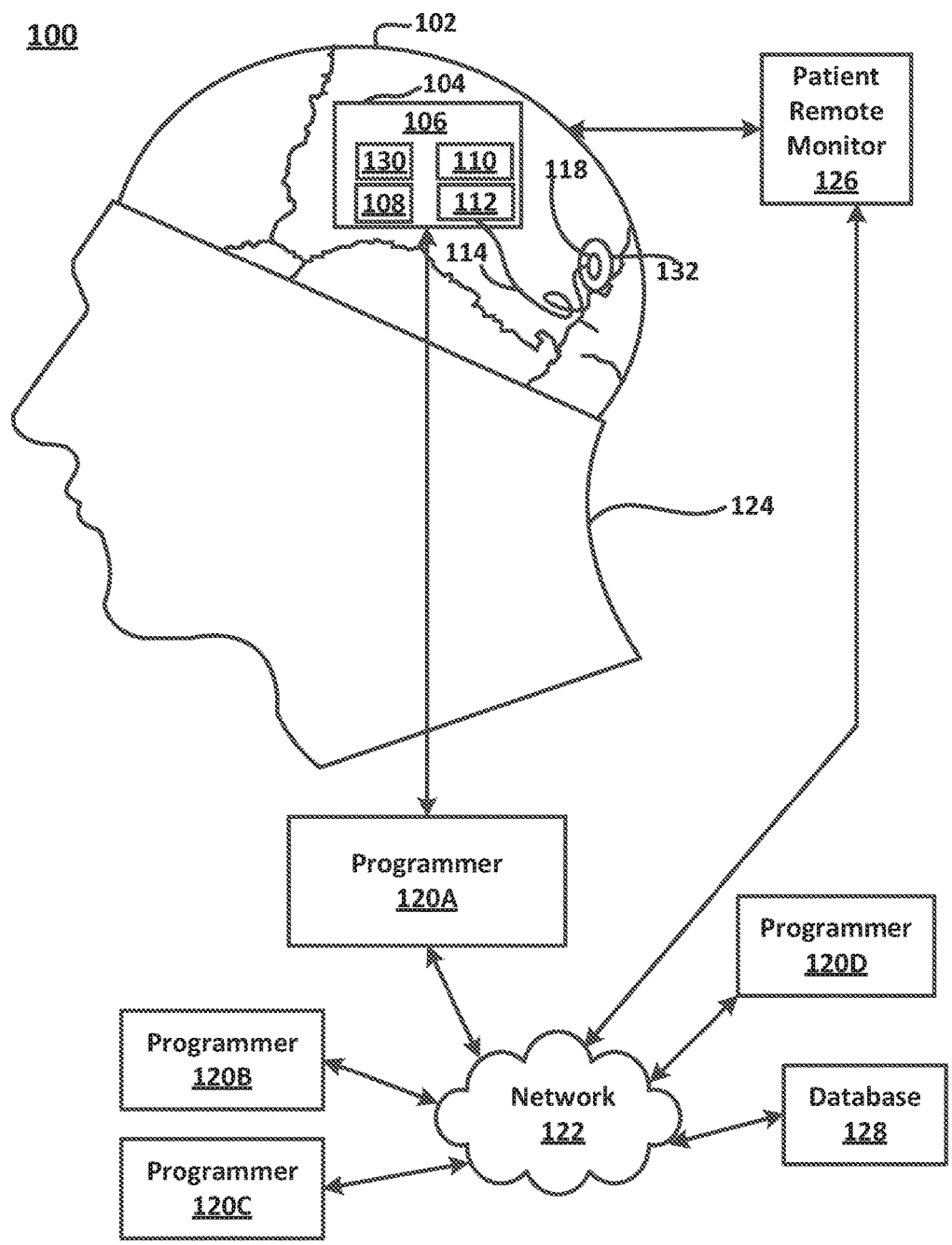
FIG. 1 is a block diagram illustrating an active implantable medical device in its use environment, implanted in a patient

The drawings referred to in this description should not be understood as being drawn to scale unless specifically.

DESCRIPTION OF EMBODIMENTS

Various embodiments are described below, with reference to detailed illustrative embodiments, in the context of active implantable medical devices and, in particular, an implantable neurostimulator. It will be apparent that the methods and systems described herein can be embodied in a wide variety of forms. Consequently, the specific structural and functional details disclosed herein are representative and do not limit the scope of embodiments.

Examples of methods and systems for selecting a state of an implantable neurostimulator that is configured to be in at least two states (e.g., "therapy disabled" and "therapy enabled") are described herein. Embodiments describe a method for unequivocally disabling or enabling the therapy a neurostimulator is programmed to deliver that is uncomplicated and requires only a simple magnet to accomplish. Some embodiments also provide a patient with auditory feedback (e.g., one or more different tones) when the neurostimulator is in one or the other of its possible states, or when the neurostimulator is susceptible of toggling between states, to facilitate a patient's (or caregiver's) ability to use a magnet to control the state of the neurostimulator.

Active implantable medical devices (i.e., devices that deliver energy or other treatment to the body) are typically provided with means for communicating with components external of the patient, such as inductive telemetry, that allows an external host to change modes or settings using various communication protocols. While inductive telemetry is most commonly used for bidirectional communication with the implant (e.g., to program a neurostimulator or to interrogate a neurostimulator to retrieve data from the implant), an active implantable medical device also often is provided with a simpler unidirectional communication protocol that involves an external magnet (manipulable by the patient or the patient's caregiver) and a sensor in the implant configured to detect the presence (or absence) of the magnet.

Implantable neurostimulators are known that are provided with a magnet sensor such as a reed switch or a giant magneto-resistive effect sensor (GMR sensor). The magnet sensor is configured so that when an external magnetic field (e.g., from an external hand-held magnet) is brought near enough to the magnet sensor, the neurostimulator will react to the presence of the magnet by disabling a therapy the neurostimulator is configured to deliver.

For example, if a patient has a movement disorder and has been implanted with a neurostimulator that is configured to deliver electrical stimulation to the patient's brain as a therapy to reduce tremors (a symptom of the patient's movement disorder), there may be times when the patient wants to disable the therapy (for example, because the patient experiences some unpleasant sensation when the stimulation is delivered [the stimulation may be at too high of an amplitude or frequency] or because the patient is going to sleep, and the patient does not notice tremors while sleeping and therefore has no desire to receive the therapy during that time).

A neurostimulator that can be disabled by a magnetic field is also desirable in certain medical situations in which it is impractical or inefficient to communicate with the implanted device using telemetry with a programmer. For instance, in an emergent situation (e.g., a patient comes into the emergency room and a caregiver tells emergency room personnel that he has an active implantable medical device, and the ER wants to subject the patient to, for example, an imaging procedure, like an MRI), being able to disable a function of the implant using a magnetic field from a readily-available magnet may be a practical alternative to using a programmer to accomplish the same thing Thus, a magnetic field may be used for some limited control over the active implant's behavior whenever it is not practical or desirable to resort to other ways of communicating between the implant and the outside world that otherwise might be available (e.g., near field or long range telemetry).

It will be appreciated that a patient may simply wish to suspend a particular therapy being delivered by an active implant for any of a variety of reasons, until the patient can get some feedback from a physician. For example, a patient with an implanted neurostimulator may think he or she is experiencing some side effect associated with the therapy, and therefore may want to stop delivery of the therapy until the patient can consult with a physician in a clinic visit (or over the telephone).

Active implantable medical devices that are configured to adjust their behavior based on the presence or absence of a magnet are known where: (1) the implant is turned off when a magnet is present and only for so long as the magnet is present (i.e., the implant's function is restored as soon as the implant no longer detects the magnet); and (2) the implant is turned off when a magnet is present for a minimum period of time and then remains off until such time as a physician can turn it back on (e.g., in an office visit).

In the first case, the patient (or the patient's caregiver) is somewhat inconvenienced insofar as the external magnet has to be held next to the implant site unless and until the patient is amenable to having the device function restored: if the patient (or caregiver) takes the magnet away, the device will come back "on." If the patient is not in a position to establish a telemetry link between the implant and the outside world (e.g., with a physician's programmer) right away, then the patient will have to be vigilant about keeping the magnet next to the implant site until some other intervention can take place.

In the second case, the patient (or patient's caregiver) may be able to satisfactorily address the issue of turning the implant off (e.g., disabling electrical stimulation therapy because of unpleasant side effects) right away by using the magnet, but if the patient wants to turn the implant back on, he or she will have to wait until a doctor's visit (or until the implant otherwise can be connected to a programmer or other external component other than the magnet) to do so.

It can also be appreciated that an active implantable medical device configured to turn off when the presence of a magnet is detected for at least a certain period of time (i.e., the second case mentioned above), in fact may turn off accidentally when the patient is in the presence of a strong enough magnetic field, even if the patient does not intend to turn the implant off. Environmental magnetic fields that might be strong enough to affect a magnet sensor in an active implantable medical device might occur in an airport (by proximity to airport security screening apparatuses) or in a hospital (by proximity to strong magnetic fields used in imaging or forms of treatment). If the particular active implant is not delivering a type of therapy that the patient typically can feel (for example, a patient may not normally feel electrical stimulation delivered to neural tissue), then the patient may have no practical way of knowing for sure whether a recent trip through airport security turned off the therapy or not.

Still other active implantable medical devices are known in which a stimulation therapy can be toggled between "on" and "off" if the implant detects a magnet. For example, if the stimulation is "on", it will be toggled "off" when a magnet is detected and vice versa (i.e., if the stimulation is "off," it will be turned "on" when a magnet is detected). This toggling behavior allows stimulation to be disabled without the patient or caregiver having to hold the magnet in place near the implant the whole time. However, if the patient or caregiver is not sure what state the implant is in just before the magnet is used to toggle the state, then it follows that the patient will not be sure what state the implant is in after the toggle. Again, in many applications of active implantable medical devices, the patient normally does not feel the therapy he or she is receiving, so the patient will not necessarily be able to tell whether the implant is delivering therapy or not.

For example, if the application is a neurostimulator configured to deliver continuous electrical stimulation therapy to treat symptoms of a movement disorder such as tremor, the patient may not be able to tell whether stimulation is on or off if the patient doesn't happen to be experiencing any symptoms directly after using the magnet. When the patient later experiences symptoms, the patient may not be whether his symptoms are getting worse despite the therapy delivered by the implant or whether his symptoms are recurring because the implant is not delivering stimulation at all. If the patient cannot tell which state the implant is in, the patient may need to visit a doctor to sort it all out (e.g., so that the physician can use a programmer to establish an inductive telemetry link to the implant and thereby turn it back on or re-enable stimulation therapy as the case may be). Thus, implants configured in this toggling second mode may also be inconvenient, especially if a particular patient is prone to over use of the magnet.

Thus it would be beneficial if the patient could be sure of what state an active implantable medical device is in (e.g., "on" or "off", "stimulation enabled" or "stimulation disabled", "stimulation at full programmed strength" or "reduced stimulation", etc.) when the patient uses the magnet in an effort to manipulate the implant. It further would be beneficial if the patient did not have to keep a magnet up against the implant site in order to be confident that the active implantable medical device was either in one state or the other.

Associating the effect a magnet has on an implant with some sort of auditory or other somatosensory feedback may be helpful, and in fact is a feature included in some of the embodiments described herein. However, incorporating this type of functionality into a system that includes an active implantable device may be associated with costs or design trade-offs that it otherwise might be desirable to avoid. Therefore, embodiments described here include magnet behavior that allows the patient or a caregiver to unequivocally establish in which state an active implant is in with a simple procedure that can be set out in a patient user manual and/or easily communicated to a patient from a "help desk" via telephone, email or a website, for example, a website using an instant messaging utility.

Overview of Discussion

The discussion begins with a description of an active implantable medical device, the behavior of which may be controlled to some degree based on a signal generated by a magnet sensor provided in the implant. More particularly, the description is directed to a specific example of an implantable responsive neurostimulator configured with a magnet sensor and magnet tracking system that controls certain behavior of the neurostimulator in the presence of a magnetic field (e.g., from an external magnet with which the patient is provided).

Active Implantable Medical Device with Tracking System for a Magnetic Field

FIG. 1 illustrates an active implantable medical device. The device is a neurostimulator 106 configured with a magnet sensor 130 such that the behavior of the neurostimulator 106 may be affected by the presence of a magnetic field applied from an external source, such as a magnet that is supplied to the patient as part of the neurostimulation system.

The neurostimulator 106 is shown implanted in a patient 124 (e g, implanted in a ferrule which is situated during a craniotomy). The neurostimulator 106 is configured to deliver a form of therapy to the patient that is intended to modulate the activity of the neural cells of the patient, such as current-controlled or voltage-controlled electrical stimulation therapy. For example, the neurostimulator 106 can be placed in operable communication with one or more electrodes (an oval-shaped single electrode 118 is shown in FIG. 1). Electrodes can be configured with the neurostimulator 106 in various stimulation pathways to deliver stimulation to the patient's tissue.

The neurostimulator 106 may be programmed to deliver stimulation to the patient continuously or on a periodic or scheduled basis. In some cases, the neurostimulator 106 may only have the capability to deliver stimulation. In other cases, the neurostimulator 106 may have more complex capabilities. For example, a neurostimulator configured as a responsive neurostimulator may have the capacity to deliver a form of therapy when it detects a pattern of activity or other "event" in one or more channels of electrographic signals continuously monitored from the patient (e.g., using leads bearing electrodes that are implanted in or on the brain). In a responsive neurostimulator, the same leads and electrodes that are used for delivering the therapy to the patient may also be used for monitoring electrographic signals from the patient.

Generally, a responsive neurostimulator is configurable to sense signals from the patient corresponding to electrical activity of the brain, to continuously monitor and process the sensed signal to identify patterns or other features of the signal or patterns and/or features associated with the signal (such as, but not limited to, the date or time the signal is sensed and/or the condition of the implantable medical device at the time a pattern or other feature is detected [e.g., whether a signal amplifier is saturated and, if so, for how long]), and to identify one or more "events" in the monitored signal when certain "detection" criteria are met (e.g., meeting or exceeding fixed or dynamic thresholds [trends)]). A responsive neurostimulation system is under investigation by NeuroPace, Inc. under the tradename "RNS SYSTEM". U.S. Pat. No. 6,016,449 to Fischell et al. for "System for Treatment of Neurological Disorders" issued Jan. 18, 2000 and U.S. Pat. No. 6,810,285 to Pless et al. for "Seizure Sensing and Detection Using an Implantable Medical Device," issued Oct. 26, 2004, also describing neurostimulation systems with responsive capabilities. U.S. Pat. Nos. 6,016,449 and 6,810,285 are incorporated by reference herein in the entirety.

The signals sensed from the patient may be monitored by a physician or other caregiver in real time, by connecting the implanted device to an external component such as a physician's programmer that is capable of communicating with the implant wirelessly, such as via telemetry. Alternatively or additionally, the neurostimulator 106 may be configured to store selected signals of the sensed signals according to certain programmed instructions. Such storage may occur periodically, whenever an event is detected, or upon command from an external component, such as a patient remote monitor 126, a physician's programmer 120A, 120B, 120C, or 120D (each of which may wirelessly communicate with the implant), or a magnet (see the magnet 220 in FIGS. 2 and 3) (the presence of which may be detected by a magnet sensor in the implant). In an application of the responsive neurostimulator 106 to diagnose and/or treat epilepsy, for example, the responsive neurostimulator 106 may be configured to detect seizures and/or seizure onsets or precursors.

The neurostimulator 106 records neurological signals, such as electrographic signals in the form of electroencephalographic (EEG) and electrocorticographic (ECoG) waveforms, detects and analyzes electrographic signals, and/or creates a log of such an analysis. In general, EEG signals represent aggregate electrical potentials related to neuronal activity within the brain detectable via sensors applied to a patient's scalp. ECoG signals, which are intracranial counterparts to the EEG signals, are detectable via sensors implanted over, on, or under the dura mater, and often within the patient's brain. Unless otherwise noted herein, the term "EEG" shall be used generically herein to refer to both EEG and ECoG signals.

The neurostimulator 106 typically has a relatively large number and variety of parameters that can be set and subsequently be modified in a programming session after the neurostimulator 106 is implanted in a patient. Thus, for example, the neurostimulator 106 may be programmed to begin recording detected EEG signals satisfying certain detection parameters or criteria (e.g., based on a combination of parameter values) from the patient 124 at the onset of ictal (seizure) activity or as a result of a prediction of ictal activity. The neurostimulator 106 may be configured to record signals or values corresponding or related to signals at times before, during and after the detection criteria have been met. The neurostimulator 106 may continue recording until the ictal activity stops. Optionally, the neurostimulator 106 saves the recording, or a sampling of it, to a memory device to preserve it for later uploading to the external device.

The neurostimulator 106 may also create a log of the ictal activity. In one example, the neurostimulator 106 records and/or logs the date and time when an event begins and ends, the duration of the event, indications of the intensity of the event, etc. The neurostimulator 106, optionally, uploads such a log to an external device, such as, but not limited to, a programmer 120A, 120B, 120C, or 120D (described in greater detail below). The neurostimulator 106 may also be configured to record and/or preserve data corresponding to EEG signals upon the initiation of some action (e.g., swiping an external magnet near the site at which the neurostimulator 106 is implanted) by the patient, a caregiver or a physician.

In some embodiments, the neurostimulator 106 detects and/or predicts any kind of neurological event that has a representative electrographic signature. While an embodiment is described herein as responsive to epileptic seizures, it should be recognized that the neurostimulator 106 can respond to other types of neurological disorders, such as movement disorders (e.g., Parkinson's disease), migraine headaches, chronic pain and neuropsychiatric disorders (e.g., depression). In various embodiments, the neurostimulator 106 detects neurological events representing any or all of these afflictions when they are actually occurring, in an onset stage, and/or as a predictive precursor before clinical symptoms begin.

Referring still to FIG. 1, the neurostimulator 106 is shown as implanted in a space or volume formed in the patient's cranium by craniotomy or other neurosurgical techniques well-known in the art (the ferrule in which the neurostimulator 106 is positioned is not shown). However, it should be appreciated that the placement described and illustrated herein is merely an example. Other locations and configurations are also possible, depending on the size and shape of the device and the patient's needs, among other factors.

Generally, the neurostimulator 106 is positioned to follow the contours of a patient's cranium 102. However, other locations within the patient's body are also possible. For example, the neurostimulator 106 may be implanted pectorally (not shown) with leads extending through the patient's neck and between the patient's cranium 102 and scalp.

With continued reference to FIG. 1, the neurostimulator 106 includes a housing 104 that encapsulates electronics that allow the desired neurological signals to be detected and/or recorded and stored and the therapy (e.g., electrical stimulation therapy) to be delivered. Other implantable components of a neurostimulation system including the neurostimulator 106 include electrode(s) 118 for monitoring or measuring electrographic signals and/or for delivering electrical stimulation to the patient's neural tissue. An electrode 118 may be formed from a platinum member. It will be appreciated that a neurostimulation system may include configuring a neurostimulator 106 to be in operable communication with sensing or stimulation elements other than electrode(s) 118.

For example, if the application of the responsive neurostimulation system is to treat epilepsy, and a seizure focus previously has been localized for the patient, the electrodes can be implanted at locations intended to capture signals generated at or near the seizure focus. Commonly, a lead bearing electrodes (e.g., lead 114) at a distal end thereof is implanted through a hole 132 drilled in the patient's skull (usually referred to as a "burr hole" because of the cranial drill used to form it). The proximal end of the lead is then connected to the neurostimulator to put the electrodes in electrical communication with the neurostimulator. It will be appreciated that elements other than electrodes may be configured and used to sense physiological data from the patient other than electrographic signals, such as optical sensors, voltammetry sensors, oximetry probes, temperature probes, and the like.

The housing 104 may be fabricated from a biocompatible material, such as, but not limited to, titanium. Titanium is light, extremely strong and biocompatible. Other biocompatible materials may additionally or alternatively be utilized in the fabrication of the housing 104.

Figure 4:
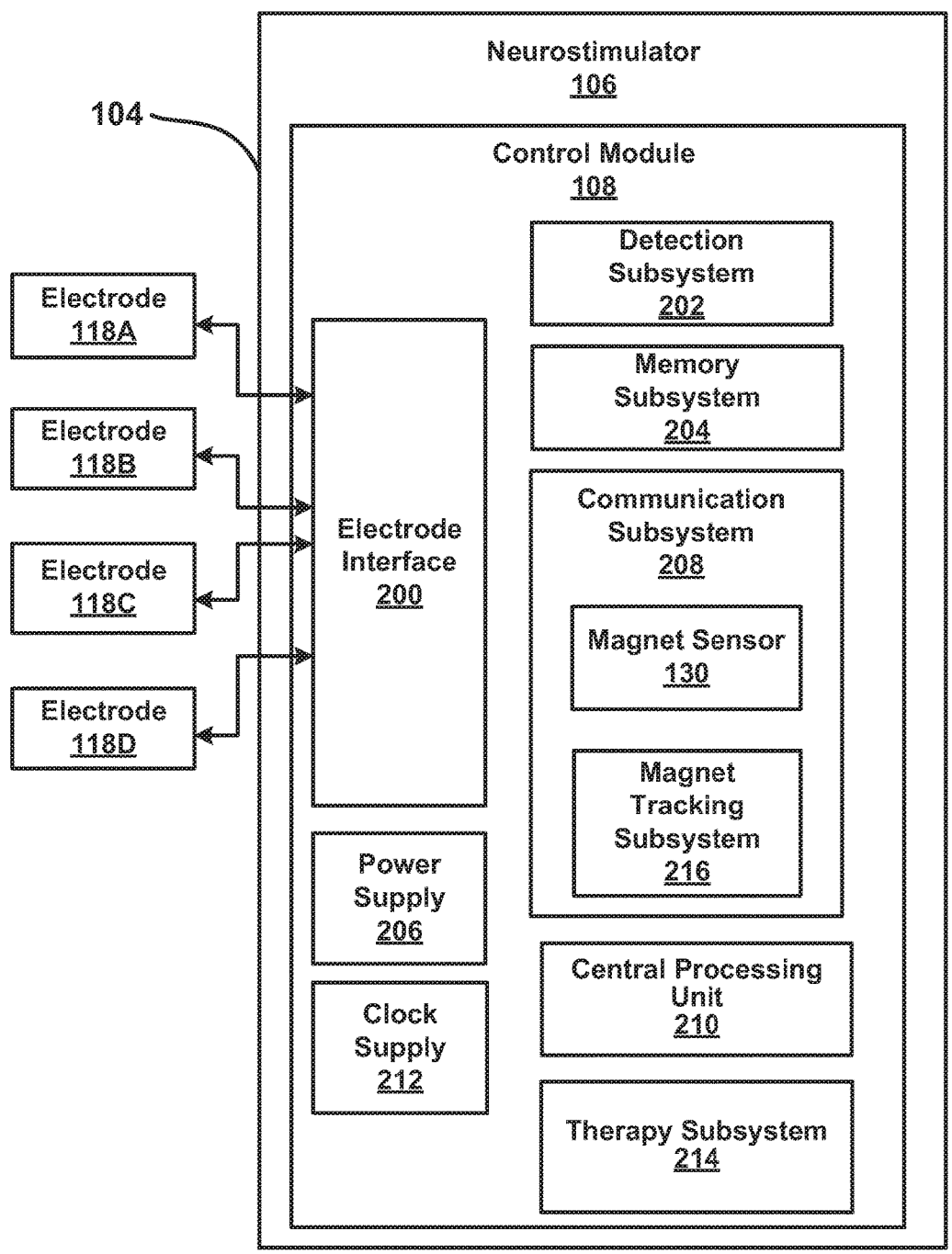
FIG. 4 is a block diagram of an implantable responsive neurostimulation system which may be used with embodiments.

The housing 104 may also enclose a battery 110 or other source of power for the neurostimulator, as well as a physical component or components that allow the neurostimulator to perform the functions represented by the blocks in the block diagram of FIG. 4. Most of the time the neurostimulator 106 will function autonomously (particularly when performing its usual sensing, detection, and recording capabilities), but the neurostimulator 106 may selectively be put in communication with a programmer or a patient remote monitor to wirelessly transmit data from the neurostimulator (i.e., to interrogate the neurostimulator and/or monitor electrographic signals from the patient in real time with an external component) or to transmit information to the neurostimulator (e.g., programming instructions, updates to code the neurostimulator uses to carry out its functions, etc.).

To enable wireless interrogation and delivery of new programming instructions to the neurostimulator, a telemetry antenna (not shown) may be provided inside or outside of the housing 104. The external devices may include devices commonly referred to as "programmers" 120A, 120B, 120C, and 120D which may be laptops or tablets or other computers with which a physician can interrogate the implant and change the programming of the implant, and a patient remote monitor 126 with which the patient can interact in some limited fashion with the implant, such as to interrogate the implant (so that data stored by the implant can be retrieved by the patient remote monitor and subsequently uploaded elsewhere, for example, over a network 122 to a central database) elsewhere.

In some embodiments, the inductive telemetry link between the implanted neurostimulator and the programmer or patient remote monitor may be established using a wand (not shown) by bringing the wand into the transmitting and receiving range of the neurostimulator 106.

Several specific capabilities and operations performed by a programmer 120A, 120B, 120C, or 120D in conjunction with the neurostimulator 106 may include, but are not limited to, the following: specifying and setting the values for parameters in the neurostimulator to adapt the function of the neurostimulator to meet the patient's needs; uploading and/or receiving data (including but not limited to EEG waveforms, logs of events detected, or data items corresponding to a condition of the device [e.g., remaining useful life of battery], that are stored on the neurostimulator); downloading and/or transmitting program code and other information; and commanding the neurostimulator 106 to perform specific actions and/or change modes, as instructed by a physician operating a programmer 120A, 120B, 120C, or 120D (hereinafter, "120", unless otherwise specifically noted). To facilitate these functions, a programmer 120 is adapted to receive physician input and provide physician output, for example, via a keypad or touch screen. Data is transmitted between a programmer 120 and the neurostimulator 106 using the wireless telemetry link.

More specifically, a programmer 120 may be selectively connected with the network 122, such as the internet, via a telemetry communication link. This allows information that is uploaded from the neurostimulator 106, as well as program code (or other information) intended for download to the neurostimulator 106, to be stored in a database 128 at one or more data repository locations (which may include various servers and network-connected programmers). This allows the patient's physician to have access to important data, including past treatment information and software updates, essentially anywhere in the world that there is a programmer (e.g., programmer 120A) or web browser (not shown) and a network connection.

A neurostimulator 106 according to embodiments has a magnet sensor 130 configured to detect a magnetic field. For example, such a magnet sensor 130 can be configured to detect the presence of a magnetic field when an external magnet is moved into the vicinity of the neurostimulator 106 by the patient 124 or a caregiver. The neurostimulator 106 may be configured to modify its behavior when the presence of the magnet is detected by the magnet sensor 130 as is described in more detail below.

Figure 3:
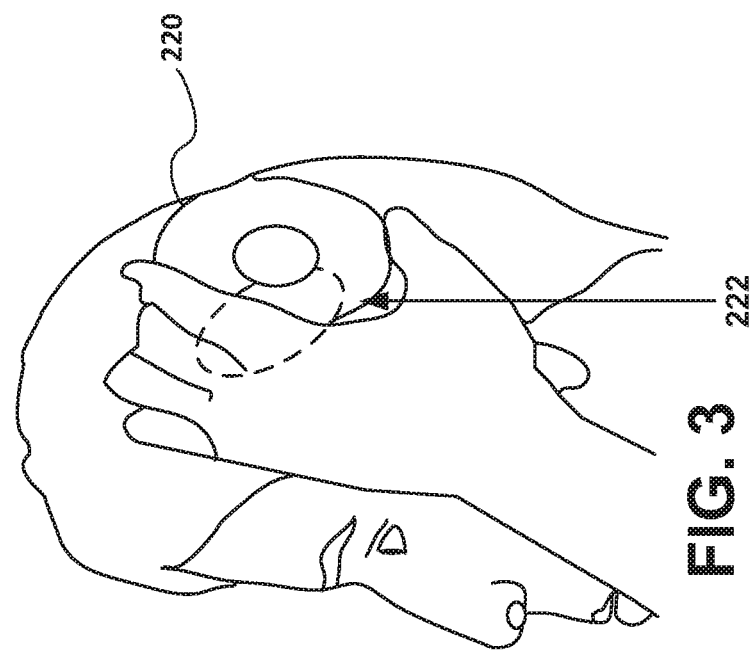
FIG. 3 is a schematic illustration of the position of an external magnet after the manipulation indicated in FIG. 2 has occurred.
Figure 2:
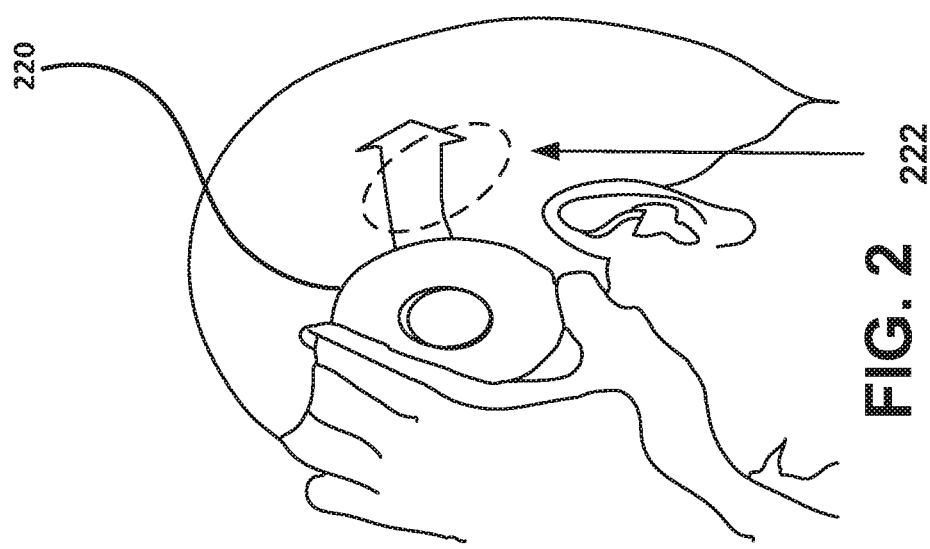
FIG. 2 is a schematic illustration of a patient manipulating an external magnet relative to the site at which an active implantable medical device has been implanted, in accordance with an embodiment.

FIGS. 2 and 3 illustrate a patient's use of an external magnet to modify the behavior of an implanted neurostimulator 106 according to embodiments. The patient brings a donut-shaped magnet 220 next to a site 222 at which the neurostimulator 106 (including the magnet sensor 130) has been implanted and then holds it there. The magnet sensor 130 may be incorporated inside the neurostimulator housing 104 or secured externally of the housing 104 but in selectable operation with the neurostimulator, for example in an enclosure separate from the neurostimulator housing that is impermeable to body fluids. The magnet sensor 130 is configured to produce a signal that corresponds to whether a magnet 220 is either present or not present.

In some embodiments, the magnet sensor 130 may be configured with a circuit (e.g., in the active implantable medical device) that provides feedback to indicate whether an external magnet is in a position relative to the implant so that the magnet will have the desired effect on the implant. The circuit may cause a tone to be generated or a visual cue to be displayed to the patient (or caregiver), such as on an external device, that allows the patient to position the magnet proximate to the implant for the best interaction between the magnet and implant.

When the implanted magnetic sensor associated with the active implantable medical device senses the presence of a magnetic field, the active implantable medical device may be configured to undertake different behaviors based on the period of time for which the implant continuously senses the magnet. For example, if the patient merely swipes the magnet over the implant, the period of time the implant senses the magnet will be very short, and this short presence of the magnet may cause the implant to undertake one of several possible actions. Which actions the implant takes may be programmable by the physician or otherwise predetermined by a manufacturer's setting in the device. In a responsive neurostimulator that is configured to record electrographic signals from a patient, a magnet swipe may cause the neurostimulator to store a record corresponding to the electrographic signals being sensed by the device at the time of the magnet swipe (or to place a marker in a record that the device is already storing at the time of the magnet swipe). When the active implantable medical device detects the presence of a magnetic field for longer periods of time, then these longer periods of time may cause the implant to undertake different behaviors as are discussed in more detail below, such as forcing the implant into one state or toggling the medical device from a state it was in just before the presence of the magnet was detected into a different state when the magnetic field is no longer detected (e.g., when the magnet 220 is taken away).

FIG. 4 is a block diagram of a responsive neurostimulator 106 of FIG. 1 as may be used for monitoring a signal generated by the magnet sensor 130. The magnet sensor 130 is configured so that its output corresponds to whether a magnetic field is or is not present relative to the neurostimulator 106. The magnet sensor output may be binary, i.e., a signal that is either at one level or another or a bit that is either a "1" or a "0". The neurostimulator 106 may be configured so that a "high" magnet sensor output corresponds to the neurostimulator 106 detecting the presence of the magnetic field and a "low" magnet sensor output corresponds to the neurostimulator 106 not detecting the magnetic field. The neurostimulator 106 may include algorithms and/or physical components or circuits for conditioning the output of the magnet sensor 130 to improve it before it is used to affect the behavior of the neurostimulator 106. For example, the neurostimulator 106 may debounce the output of the magnet sensor 130 before allowing a state change of the neurostimulator 106 based on the magnet sensor 130 output to occur.

The various functions of the neurostimulator 106 can be described with reference to a control module 108 that allows the implant to interface with elements for delivering a therapy to the patient and with the outside world. In the responsive neurostimulator 106, the control module 108 may also be configured to interface with elements for sensing physiological data (such as electrographic signals) from the patient. In some responsive neurostimulators, the same elements can be used for sensing physiological data and delivering therapy. For example, in the responsive neurostimulation system under investigation by NeuroPace, Inc. under the trade name "RNS SYSTEM", the control module of the neurostimulator interfaces with electrodes that are also implanted in the patient and which the neurostimulator can configure either as sensing elements or as stimulation elements.

In FIG. 4, an electrode interface 200 of the control module 108 functions to select which electrodes (of the electrodes 118A, 118B, 118C, and 118D [hereinafter, "electrode 118", unless otherwise noted]) are used by the neurostimulator 106 in which configurations and for which purposes (e.g., sensing data from the patient or delivering therapy to the patient).

The control module 108 is provided with a self-contained power supply 206 (which may be a primary cell or rechargeable battery) that supplies the voltages and currents necessary for each of the other subsystems of the neurostimulator 106 to carry out its intended function(s), and a clock supply 212 which supplies needed clock and timing signals.

The control module 108 is provided with a memory subsystem 204 and a central processing unit (CPU) 210, which can take the form of a microcontroller.

The central processing unit 210 controls a therapy subsystem 214 which is configured to output a form of therapy (e.g., electrical stimulation therapy) to the patient, for example, via the electrode interface 200 and then one or more of the electrodes 118. (The electrode interface 200 may also encompass charge-balancing and other functions required for a proper interface with neurological tissue.) The communication subsystem 208 allows the implanted neurostimulator 106 to communicate with the outside world. For example, the communication subsystem 208 is provided with a magnet sensor 130 and a magnet tracking subsystem 216 so that the neurostimulator 106 can recognize and adjust its behavior based on the presence or absence of a magnetic field from a magnet applied externally of the implant (see, e.g., FIG. 2).

The communication subsystem 208, via the central processing unit 210 or otherwise, may cause the memory subsystem 204 to record and store one or more data items relative to the magnet sensor 130 and magnet tracking subsystem 216, such parameters the values of which correspond to the number of times the magnet sensor 130 detected the presence of a magnetic field, or the times the neurostimulator 106 changed its state based on the presence of the magnet and into which state the neurostimulator 106 transitioned, or the times the neurostimulator 106 was forced into one state or the other. Similarly, the neurostimulator 106 may be configured so that the memory subsystem 204 records and stores parameters the values of which correspond to some other action the presence of the magnet caused the neurostimulator 106 to take based on the presence of the magnet (such as storing an electrographic signal or placing a marker in a record of an electrographic signal). The communication subsystem 208 and/or the magnet tracking subsystem 216, in one embodiment, includes a timer that tracks a time period over which the magnet sensor continuously detects the magnetic field. The timer starts tracking time when the presence of the magnetic field is detected and stops tracking time when the presence of the magnetic field is no longer detected. In one embodiment, the communication subsystem 208 and/or the magnet tracking subsystem 216 includes a comparator that compares an elapsed time calculated by the timer, wherein the elapsed time corresponds to the period over which the magnetic field is detected to a first endpoint, a second endpoint, and an interval extending between the first and second endpoints (as will be described below).

Typically, the communication subsystem 208 includes a telemetry antenna (which may be situated inside or outside of the neurostimulator housing) enabling the transmission and reception of signals, to and/or from an external apparatus, via inductive coupling. One external apparatus may comprise a programmer 120 that is used by a physician to optimize the performance of the neurostimulator 106 for the particular patient, in part, by setting the values of the parameters that are used by the neurostimulator 106 to control the delivery of therapy and the response of the neurostimulator 106 to the presence of a magnetic field.

Alternative embodiments of the communication subsystem 208 may use an antenna for an RF link or an audio transducer for an audio link to the patient 124, in order to provide indications of neurological events, a system's status, and/or other relevant information.

In a responsive neurostimulator, the control module 108 also may include a detection subsystem 202, which operates on signals corresponding to data sensed from the patient and routed from the electrodes 118 through the electrode interface 200. (The electrode interface 200 may act as a switch to select which electrodes 118 to sense physiological data from and may encompass other functions such as signal conditioning and processing including amplification and isolation).

The detection subsystem 202 may include an EEG analyzer function. The EEG analyzer function may be adapted to receive EEG signals from the electrode 118, through the electrode interface 200, and to process those EEG signals to identify neurological activity indicative of a seizure, an onset of a seizure, and/or a precursor to a seizure.

The detection subsystem 202 also may contain further sensing and detection capabilities, including but not limited to, parameters derived from other physiological conditions (such as electrophysiological parameters, temperature, blood pressure, movement, etc.).

The detection subsystem 202 is coupled with both the central processing unit 210 and the memory subsystem 204 so that data representative of sensed EEG signals can be recorded and stored.

It should be noted that while the memory subsystem 204 is illustrated in FIG. 4 as a separate functional subsystem, the other subsystems might also use various amounts of memory to perform the functions described herein, as well as other functions. Further, while the control module 108 may be a single physical unit contained within a single physical enclosure, namely the housing 104, this does not need to be the case and the control module 108 may be configured differently. The control module 108 may be provided as an external unit not adapted for implantation, or it may include a plurality of spatially separate units, each performing a subset of the capabilities described above. Also, it should be noted that the various functions and capabilities of the subsystems of the neurostimulator 106, including the communications subsystem 208 and its magnet tracking system 216 may be performed by electronic hardware (e.g., hard wired modules), computer software (or firmware), or a combination thereof. The division of work between the central processing unit 210 and other functional subsystems may also vary. The functional distinctions illustrated in FIG. 4 may not reflect the integration of functions in a real-world system or method according to the embodiments disclosed herein.

In one embodiment, the neurostimulator 106 is provided with magnet sensor 130, such as a giant magnetoresistance or "GMR" sensor, that is configured to generate a signal that is a function of whether the magnet sensor 130 senses the presence of a magnetic field. The signal generated by the magnet sensor 130 may be processed or conditioned using techniques well known in the art such as debouncing, before it is used to control the behavior of the neurostimulator.

The patient is provided with a magnet, for example, the donut-shaped magnet 220 shown in FIGS. 2 and 3 which produces a magnetic field strong enough to be recognized by the magnet sensor 130 when the magnet 220 is brought into close enough proximity to the neurostimulator 106. Implementations of magnet sensors other than that using a GMR sensor will be apparent, such as reed switches and the like.

A magnet tracking system 216 included in the neurostimulator 106 is configured to initiate action based on whether the magnet sensor 130 generates a signal corresponding to the presence of a magnet, including actions that change the behavior of the neurostimulator 106. More particularly, and according to one example, the magnet tracking subsystem 216 may initiate action either (1) to disable the therapy subsystem 214 from delivering whatever therapy it might be programmed to deliver to the patient or (2) to toggle the state of the neurostimulator 106 from a state in which therapy is disabled to a state in which therapy is enabled or vice versa.

Depending on how long a magnet sensor 130 detects the presence of a magnetic field, the magnet tracking subsystem 216 may cause the neurostimulator 106 to stay in the state the neurostimulator 106 was in just before the presence of the magnet was detected; transition from the state the neurostimulator 106 was in just before the presence of the magnet was detected to a different state; or transition into or remain in, as the case may be, a predetermined one of the two states. In the example described herein, the two possible states of the neurostimulator 106 into which the magnet can transition the neurostimulator 106 are a state in which therapy is enabled and a state in which therapy is disabled.

It will be appreciated that it may be desirable for the neurostimulator 106 to behave in the presence of the magnet by transitioning to and from states other than "therapy enabled" and "therapy disabled" states, for example, depending upon the application of the neurostimulator 106. If the neurostimulator 106 is being used to deliver a form of continuous therapy to the patient, use of the magnet may cause the neurostimulator 106 to transition from a state in which it is delivering a higher level of stimulation to a state in which it is delivering a lower level of stimulation or a state in which it is in a stand-by mode. In other circumstances, use of the magnet may cause the medical device to transition from a state corresponding to some level of activity to a state in which the device is completely off.

As will be discussed below, embodiments enable a patient to change a state of a neurostimulator 106 deterministically or with certainty, using a magnet. A patient (or caregiver) can cause the neurostimulator 106 to go into a "therapy disabled" state by holding the magnet over the implant for a long enough period of time, without having to be concerned about the state the neurostimulator 106 was in just before the magnet was applied. Further, once the patient (or caregiver) knows the neurostimulator 106 is in the "therapy disabled" state, he or she can return the neurostimulator 106 to a "therapy enabled" state by following a simple procedure with the magnet.

These embodiments described here may be contrasted with other approaches to determining and/or changing a state of a neurostimulator in which the patient is required to continuously hold the magnet over the implant in order to ensure therapy is disabled, or in which a physician or other health care provider is required to assist with changing the state of the implant, or in which the patient is left unsure, after using a magnet, as to exactly which state the implant is in (e.g., because the result of applying the magnet depends on what state the neurostimulator was in just before the magnet was applied, and the patient may not be certain what that prior state was). Thus, embodiments provide a method and system for using an external magnet to both select a state of a neurostimulator that is configured to be in at least two states and ensure a state of a neurostimulator.

Example Method for Selecting a State of an Active Implantable Medical Device

Embodiments provide a method for using an external magnet to unequivocally change a state of an active implantable medical device. In particular, an example is described for a system and method for changing the state of a neurostimulator to disable and enable a therapy the neurostimulator is configured to deliver to a patient (e.g., electrical stimulation therapy). In other embodiments and as noted above, the behavior of the neurostimulator relative to use of the magnet may be to transition the neurostimulator between states other than "therapy disabled" and "therapy enabled." In still other embodiments, the active implanted medical device need not necessarily be a neurostimulator. Embodiments also provide an auditory feedback feature that can be relied upon together with the magnet to further enhance the patient's (or the caregiver's) degree of certainty with respect to the experience (i.e., as to whether the implant is in one state or another).

Figure 5:
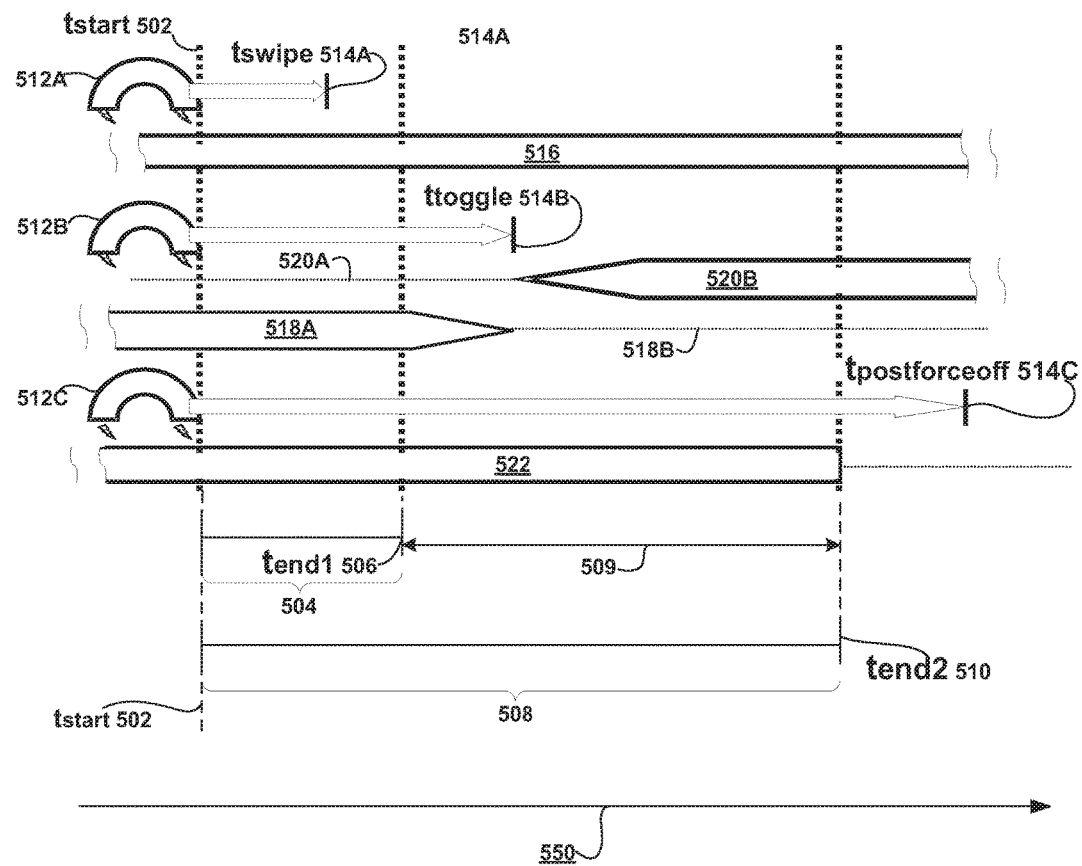
FIG. 5 is a timing diagram illustrating a sequence of events in a method for selecting a state of an active implantable medical device that is configured to be in at least two states, in accordance with embodiments.
Figure 6:
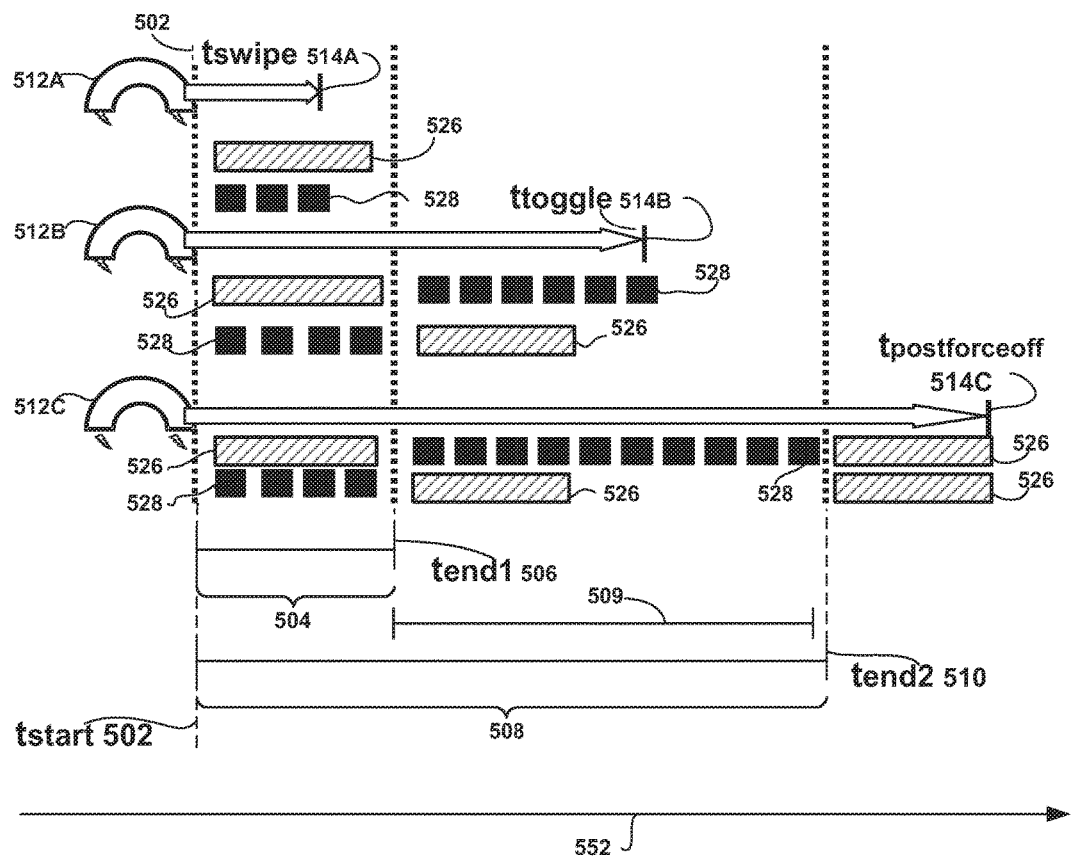
FIG. 6 is a timing diagram illustrating a feature of generating auditory feedback in a method for selecting a state of an active implantable medical device that is configured to be in at least two states, in accordance with other embodiments.

Referring to FIGS. 5 and 6, a sequence of events corresponding to the behavior of an implanted neurostimulator relative to the presence of an external magnetic field, such as provided by a magnet 220 (FIG. 2) will now be described. In sum, the timing diagram reflects what the neurostimulator 106 does after it begins to detect a magnetic field and then it either ceases to detect the magnetic field or a certain time interval is exceeded.

In FIG. 5, the neurostimulator 106 may detect the presence of a magnetic field (e.g., because the patient is holding a magnet next to the implant site so that the presence of the magnetic field is detected by a magnet sensor 130 in the neurostimulator 106) for a first interval, referred to as a "magnet toggle interval" 504, and for a second interval, referred to as a "magnet force off interval" 508.

In an example, if the patient holds a magnet in proximity to the implanted neurostimulator 106 for a time longer than the magnet toggle interval 504 and at least as long as the magnet force off interval 508, the neurostimulator 106 will disable therapy, regardless of whether therapy was enabled or disabled just before this particular application of the magnet.

On the other hand, if the patient holds a magnet next to the neurostimulator 106 longer than the magnet toggle interval but for a time that is less than the end of the magnet force off interval (i.e., the time period 509 in FIG. 5), the neurostimulator 106 will toggle the state of therapy as soon as the neurostimulator 106 stops detecting the magnetic field; that is, the neurostimulator 106 will enable therapy if it was disabled just before this particular application of the magnet, and will disable therapy if it was previously enabled just before this particular application of the magnet.

It will be appreciated that if the neurostimulator 106 first is forced into the "therapy disabled" state by reason of the fact that the neurostimulator 106 detected the presence of a magnetic field continuously throughout the end of the magnet force off interval (e.g., by holding the magnet over the implant through and including the end of the magnet force off interval), then the patient or the patient's caregiver will be assured that therapy is disabled. If the patient then wants to make sure therapy is enabled, the patient can hold the magnet over the implant long enough to get past the magnet toggle interval and then remove it before the end of the magnet force off interval. Now, the patient will know the implant is in the "therapy enabled" state because when the magnet was removed during the time period in which the neurostimulator 106 was susceptible of toggling, the neurostimulator 106 toggled from the "therapy disabled" state to the "therapy enabled" state.

Each of the magnet toggle interval 504 and the magnet force off interval 508 may be defined as parameters with parameter values in an algorithm for determining a behavior of the neurostimulator 106 in response to the neurostimulator 106 detecting the presence of a magnetic field, such as the behavior to disable therapy. The neurostimulator 106 may implement this algorithm, for example, as part of the function of the "magnet tracking subsystem" indicated in the block diagram of FIG. 4.

In this description, the duration of each of the magnet toggle interval 504 and the magnet force off interval 508 are both measured or calculated from a common starting point, namely, $t_{start}$ 502. Alternatively, the duration of each interval may be defined with reference to unique start and end times along the axis 550 corresponding to units of time, for example, the start time of the magnet force off interval may occur at the end time of the magnet toggle interval.

It should also be appreciated that embodiments provide a simple, deterministic two-step procedure to enable stimulation. Put another way, even if the patient is not sure which state the neurostimulator 106 is in when the process is started, the patient will be sure which state the neurostimulator 106 is in when the process ends, namely (in this example), a "therapy enabled" state. This deterministic two-step procedure is described as follows: (1) applying the magnet for longer than the magnet force off interval 508 (longer than the endpoint at the time $t_{end2}$ 510), in which case the neurostimulator 106 will be transitioned into a "therapy disabled" state if the neurostimulator 106 was not in that state already; and (2) removing the magnet and reapplying the magnet for longer than the magnet toggle interval 504 (longer than the endpoint at the time $t_{end1}$ 506), but removing the magnet again before the end of the magnet force off interval 508 (i.e., removing the magnet again between the end of the magnet toggle interval 504 and the end of the magnet force off interval 508 (between the endpoint at the time $t_{end1}$ 506 endpoint at the time $t_{end2}$ 510.

The length of the magnet toggle interval 504 and the magnet force off interval 508 and the effect each interval has relative to the patient's (or caregiver's) use of a magnet 220 may be fixed (as in manufacturer settings for the device) and set forth in a patient manual provided at the time the active implantable medical device is implanted. Alternatively, the instructions relevant to using a magnetic field to ensure that an active implanted medical device is either in one state or another may be made available over a website, or communicated in some sort of training related to the implant. In some circumstances, a patient or caregiver may be able to call a "Help Desk" or a doctor's office and ask someone to guide them through the procedure to first make sure the implant is in one state (e.g., the "therapy disabled" state) and, if desired, then to make sure the implant is in the other state (e.g., the "therapy enabled" state).

Thus, for example, the features of some embodiments that allow a magnet to be used to make sure a neurostimulator's therapy is disabled may be relied upon not only by patients and their regular caregivers, but also in emergent situations. For instance, emergency room personnel familiar with the neurostimulator's behavior relative to a magnetic field may be able to use a magnet to disable a patient's therapy while the ER personnel are trying to diagnose or treat the patient.

In still other embodiments, one or both of the values that determine the length of the magnet toggle interval 504 and the magnet force off interval 508 may be programmable by a physician and thus tailored for specific patients. A physician may select values for each of the intervals by interacting with the patient's implant using a programmer, such as a programmer 120A, and a wireless communications link to the implant. When the values are programmable, the values of course will have to be communicated in an appropriate manner to the patient and/or the patient's caregivers, so that the patient will know how long the implant has to detect the presence of the magnetic field for the implant to be forced into a first state and then for how long the implant has to detect the presence of the magnetic field for the implant to be susceptible of toggling into a second state so that, when the magnetic field is removed, the implant will transition into the second state.

In a typical case, the magnet force off interval 508 will be considerably longer than the magnet toggle interval 504. For example, a magnet force off interval 508 may be defined by values for relevant parameters as being twenty seconds long, and a corresponding magnet toggle interval 504 may be defined by relevant parameters as being only five seconds long. Thus, when the magnet is held near the neurostimulator 106 for a relatively long duration (i.e., longer than the magnet force off interval 508), the stimulation is disabled deterministically; that is, the stimulation is disabled whether or not it was enabled or disabled just prior to application of the magnet at the time $t_{start}$ 502. Subsequently, when the magnet is removed and then again held near the neurostimulator 106 for a shorter duration before it is again removed (i.e., for longer than magnet toggle interval 504 but for less than the whole of the magnet force off interval 508 (or removed between the endpoint at the time $t_{end1}$ 506 but a time less than the endpoint at the time $t_{end2}$ 510)), the stimulation is deterministically enabled. In other words, after following this procedure, the stimulation is enabled, regardless of whether it enabled or disabled just before the two-step procedure was undertaken.

A method according to embodiments will now be described more particularly with reference to the top, middle and bottom panels of FIG. 5, where time is represented by the x-axis 550. In each panel of FIG. 5, the active implantable medical device begins to detect the presence of a magnetic field at the time $t_{start}$ 502. In the top panel 512A, the active implantable medical device ceases to detect the presence of a magnetic field at a time $t_{swipe}$ 514A, which occurs before the end point of the magnet toggle interval 504 at the time $t_{end1}$ 506. As described above, if the implant detects the magnet for less than the magnet toggle interval 504, the implant will not change state: it will remain in whatever state it was in at the time $t_{start}$ 502 (A transient detection of a magnetic field by the implant may cause nothing at all to happen. However, in some embodiments, the presence of the magnetic field for less than the magnet toggle interval 504 may cause the implant to do something other than change states, however, as is described in more detail below in connection with the discussion of a "magnet swipe.") The unchanged state of the active implantable medical device is indicated graphically by the bar 516.

In the middle panel 512B, the active implantable medical device ceases to detect the presence of a magnetic field at a time $t_{toggle}$ 514B. Since the time $t_{toggle}$ 514B occurs in the time period 509, after the magnet toggle interval 504 has ended (at the time $t_{end1}$ 506) and before the magnet force off interval 508 has ended (at the time $t_{end2}$ 510), the failure of the implant to continue to detect the magnetic field will cause the implant to transition from a first state to a second state (e.g., from a "therapy disabled" state to a "therapy enabled" state or vice versa). In other words, if the active implantable medical device ceases to detect the magnetic field during the time period 509, and the implant was in the first state at the beginning (at time $t_{start}$ 502), then it will change to the second state at the time $t_{toggle}$ 514B. This transition from the first state to the second state is indicated graphically by line 520A and bar 520B. On the other hand, if the active implantable medical device ceases to detect the magnetic field during the time period 509 and the implant was in the second state when the magnetic field began to be detected (at time $t_{start}$ 502), then the implant will transition to the first state at the time $t_{toggle}$ 514B. This transition from the second state to the first state is indicated graphically by bar 518A and line 518B.

In the bottom panel 512C, the active implantable medical device ceases to detect the presence of a magnetic field at a time $t_{postforceoff}$ 514C. Since the time $t_{toggle}$ 514B occurs in the time period 509, after the magnet force off interval 508 has ended (at the time $t_{end2}$ 510), then the active implantable medical device will be forced into designated one of the first or second states (e.g., forced into a "therapy disabled" state) as soon as the time $t_{end2}$ 510 is exceeded. The state of the neurostimulator, which is forced to be a designated state at time $t_{end2}$ 510, is indicated graphically by bar 522. In this example, as long as the time $t_{end2}$ 510 is exceeded, it does not matter when the implant thereafter stops detecting the magnetic field (e.g., a magnet 220 being manipulated by the patient or caregiver), the implant will be in the designated state if the magnetic field remains in place for longer than $t_{end2}$ 510 (e.g., longer than the time $t_{postforceoff}$ 514C, or shorter than the time $t_{postforceoff}$ 514C but at least as long as the time $t_{end2}$ 510).

While embodiments may be configured so that the default behavior of the neurostimulator 106 during the time period 509 when the neurostimulator 106 is to be susceptible of toggling (from whichever state it was in just before the magnetic field was detected to a different state if the magnetic field is no longer detected by the magnet sensor 130 [i.e., if the magnet 220 is taken away]), there may be circumstances under which it is not desirable to allow a magnetic field to enable the neurostimulator 106 to deliver therapy. Thus, in some embodiments, the neurostimulator 106 may be provided with a parameter or parameters, programmable by a physician using a programmer 120, which will have the effect of disabling the state changing behavior of the neurostimulator 106 based on the presence or absence of a magnetic field. In other words, a physician may want to turn a patient's therapy off and not allow the patient to turn it back on using the magnet.

This may be the case where the patient is participating in a "sham" or "placebo" arm of a clinical trial, in which therapy is temporarily turned off and in which, if therapy were to be enabled, the scientific data derived from the patient would be compromised. Similarly, if the neurostimulator 106 has the capacity to sense and record and store electrographic signals from the patient as well as to deliver a form of electrical stimulation therapy to the patient (e.g., a responsive neurostimulator), the physician may wish to leave the sensing, recording and storing functions in operation but to disable the stimulation until such time as the physician is able to diagnose what is happening with the patient and then use the diagnosis to decide upon a course of stimulation therapy. In this case, the physician may want the patient to still be able to use a magnet 220 for "magnet swipes" to cause the neurostimulator 106 to record electrographic signals (or to mark records of electrographic signals) (discussed further below), but the physician may not want the patient to be able to use the magnet to transition the neurostimulator 106 into a "therapy enabled" state.

An implantable neurostimulator 106 may be programmed to block the ability for a detected magnetic field to change the state of a neurostimulator 106 from a "therapy disabled" to a "therapy disabled" state by, for example, setting the values for the magnet toggle interval 504 and the magnet force off interval 508 to 0 s, or by otherwise preventing the neurostimulator 106 from transitioning into a "therapy enabled" state whenever the magnet sensor 130 detects a magnetic field.

In other embodiments, once an implantable neurostimulator 106 has changed states from "therapy disabled" to "therapy enabled" or vice versa some maximum amount of times, the implantable neurostimulator 106 may be controlled by a parameter that either disables additional state changes from "therapy disabled" to "therapy enabled" or only allows a transition into a state other than a "therapy enabled" state from a "therapy disabled" state. For instance, a physician may program a patient's neurostimulator 106 so that, after a patient (or caregiver) has caused the implant to change from "therapy enabled" to "therapy disabled" five times in a single day, further detection of the presence of a magnetic field will under no circumstances allow therapy to be enabled (e.g., until the patient talks to his or her physician to confirm that the toggle behavior is desired and is not the undesired result of, for instance, strong environmental magnetic fields in the patient's workplace). Alternatively, after excessive toggling between states (e.g., more than 20 times), when the neurostimulator 106 next detects the presence of a magnetic field rather than toggling from a "therapy disabled" state to a "therapy enabled" state, the neurostimulator 106 may change to a state in which some nominal level of therapy (i.e., not the "full strength" therapy corresponding to the "therapy enabled" state) is delivered, until a physician can be consulted about the situation. In some embodiments, the parameters that control whether the presence of a magnetic field will allow the neurostimulator 106 to changes states at all, or that will condition state changes based on some other criteria may be programmed using a physician programmer or some other external component configured to communicate with the implant.

As described above, an active implantable medical device according to embodiments may be configured to undertake action other than transitioning between one state to another upon detecting a magnetic field with its magnet sensor 130. In some embodiments, when a neurostimulator 106 detects the presence of a magnetic field beginning at time $t_{start}$ 502 but for less than the end of the magnet toggle interval 504 (i.e., before time $t_{end1}$ 506), the neurostimulator 106 will not change from a "therapy disabled" state to a "therapy enabled" state or vice versa, but a "magnet swipe" before time $t_{end1}$ 506 may cause the neurostimulator 106 to take some other action. For example, the neurostimulator currently under investigation under the name "RNS SYSTEM" neurostimulator for NeuroPace, Inc. may monitor electrical activity sensed from the patient's brain and may record some of that activity in records that are stored, at least temporarily, in a memory in the neurostimulator. The neurostimulator 106 may also record and store information about what the neurostimulator 106 is doing at a particular time during its operation (e.g., the time and date a particular record of electrical activity was created and/or stored, an item of information corresponding to the remaining battery life of the implanted power source, whether or not the device was capable of delivering neurostimulation to the patient at the level at which it was programmed to deliver the stimulation, etc.).

In situations in which the neurostimulator 106 has features similar to the aforementioned features for sensing electrical activity and/or creating records and storing the records of the electrical activity and recording and storing "device diagnostics"-type information corresponding to information about the behavior of the device itself (as distinguishable from the electrical activity of the patient which the device is monitoring), a "magnet swipe" in the period between the time $t_{start}$ 502 and the time $t_{end1}$ 506 (i.e., in which removal of the magnet occurs before the end of magnet toggle interval 508 after which the neurostimulator 106 becomes susceptible of toggling from the state it is in to a different state) may, for example, cause one or more of the following to occur: (1) causing the neurostimulator 106 to store in its memory a record corresponding to the electrical activity the neurostimulator 106 was sensing at some point during that magnet detection period; (2) causing the neurostimulator 106 to store in its memory one or more values corresponding to the date and a time when the magnet was detected (e.g., a time during the magnet detection period corresponding to a particular "magnet swipe"); and (3) causing the neurostimulator 106 to introduce some form of a marker into a record of electrographic activity being created in the neurostimulator 106 at some point during that magnet detection period (e.g., a marker indicating that the patient swiped the magnet at a particular point during the recording of the neurostimulator 106).

FIG. 6 is similar to the timing diagram of FIG. 5 illustrating the behavior of a neurostimulator 106 relative to the use of a magnet when the magnet is applied at a time $t_{start}$ 502 and then removed (1) before a time $t_{end1}$ 506 at the endpoint of a magnet toggle interval 504 (top panel 512A); (2) after the time $t_{end1}$ 506 at the endpoint of a magnet toggle interval 504 but before a time $t_{end2}$ 510 at the endpoint of a magnet force off interval 508 (middle panel 512B); and (3) after the time $t_{end2}$ 510 at the endpoint of a magnet force off interval 508 (bottom panel 512C). However, in FIG. 6 the additional feature of auditory feedback is illustrated, to convey that, in accordance with some embodiments, the magnet tracking system 216 may be associated with one of two auditory tones that are generated to guide the patient as to which state the neurostimulator 106 is in or to which state the neurostimulator 106 will transition if the neurostimulator 106 ceases to detect the magnetic field (i.e., which state the neurostimulator 106 will go into if the magnet is removed.) More particularly, in an example, the "therapy disabled" state is associated with a long, low tone which is represented by the shaded blocks 526 in FIG. 6. The "therapy enabled" state is associated with a series of beeps, which are represented by the strings of solid black rectangles 528 in FIG. 6. In one embodiment, the auditory feedback is generated by a feedback signal generator such as a piezoelectric element driven by an oscillator circuit or digital waveform generator.

Referring now to the top panel 512A of FIG. 6, if the neurostimulator 106 detects the presence of a magnetic field at time $t_{start}$ 502 and the neurostimulator 106 is then in a "therapy disabled" state, then the patient will hear the long, low tone 526. In this example, the neurostimulator 106 ceases to detect the magnetic field at time $t_{swipe}$ 514A. When the magnetic field is no longer detected, the neurostimulator 106 remains in the "therapy disabled" state and stops generating the long, low tone 526. In another embodiment, the long, low tone 526 continues for a predetermined length of time or for a length of time determined by a programmed setting.

Referring now to the middle panel 512B of FIG. 6, if the neurostimulator 106 continues to detect the presence of the magnetic field throughout the magnet toggle interval 504 (i.e., until the time $t_{end1}$ 506) then the long, low tone 526 will continue to be generated. Then, at the end of the magnet toggle interval 504, the neurostimulator 106 will become susceptible of toggling from the "therapy disabled" state to a "therapy enabled" state up until the end point of the magnet force off interval 508 (i.e., up until the magnetic field is detected beyond the time $t_{end2}$ 510). In the example of FIG. 6, the neurostimulator 106 stops detecting the magnetic field at the time $t_{toggle}$ 514B (e.g., because the patient has taken a magnet 220 away from the location of the implant). Throughout the time the neurostimulator 106 is susceptible of toggling from the "therapy disabled" state to the "therapy enabled" state, the beeps 528 will be generated. This will let the patient know that if the magnetic field is removed (e.g., if the patient takes the magnet away), then the neurostimulator 106 will toggle into the "therapy enabled" state from the "therapy disabled" state.

Referring now to the bottom panel 512C of FIG. 6, if the neurostimulator 106 continues to detect the presence of the magnetic field throughout all of the magnet toggle interval 504 and all of the magnet force off interval 508 (i.e., from the time $t_{start}$ 502 through and including the time $t_{end2}$ 510), then the long, low tone 526 will be generated for the entirety of the magnet toggle interval 504 (from the time $t_{start}$ 502 to the time $t_{end1}$ 506), the beeps 528 will be generated during the time period 509 (between the magnet toggle interval endpoint time $t_{end1}$ 506 through the magnet force off interval endpoint time $t_{end2}$ 510), and then the long, low tone 526 will be generated again as soon as the magnetic field has been detected long enough to force the neurostimulator 106 into the "therapy disabled" state. When the neurostimulator 106 ceases to detect the magnetic field (at time $t_{postforeoff}$ 514C in FIG. 6), neither the long, low tone 526 nor the beeps 528 are generated.

FIG. 6 also illustrates the opposite case for the various timing scenarios for when the neurostimulator 106 detects and ceases to detect the presence of a magnetic field. Referring again to the top panel 512A of FIG. 6, if the neurostimulator 106 detects the presence of a magnetic field at time $t_{start}$ 502 and the neurostimulator 106 is then in a "therapy enabled" state, then the patient will begin to hear the series of beeps 528. When the neurostimulator 106 ceases to detect the magnetic field at time $t_{swipe}$ 514A, the neurostimulator 106 remains in the "therapy enabled" state and stops generating the beeps 528.

Referring now to the middle panel 512B of FIG. 6, if the neurostimulator 106 continues to detect the presence of the magnetic field throughout the magnet toggle interval 504 (i.e., until the time $t_{end1}$ 506) and if the neurostimulator 106 was in a "therapy enabled" state at time $t_{start}$ 502, then the beeps 528 will continue to be generated. Then, at the end of the magnet toggle interval 504, the neurostimulator 106 will become susceptible of toggling from the "therapy enabled" state to a "therapy disabled" state up until the end point of the magnet force off interval 508 (i.e., up until the magnetic field is detected beyond the time $t_{end2}$ 510). In the example of FIG. 6, the neurostimulator 106 stops detecting the magnetic field at the time $t_{toggle}$ 514B (e.g., because the patient has taken a magnet 220 away from the location of the implant). Throughout the time the neurostimulator 106 is susceptible of toggling from the "therapy enabled" state to the "therapy disabled" state, the long, low tone 526 will be generated. This will let the patient know that if the magnetic field is removed (e.g., if the patient takes the magnet away), then the neurostimulator 106 will toggle into the "therapy disabled" state from the "therapy enabled" state.

Referring now to the bottom panel 512C of FIG. 6, if the neurostimulator 106 continues to detect the presence of the magnetic field throughout all of the magnet toggle interval 504 and all of the magnet force off interval 508 (i.e., from the time $t_{start}$ 502 through and including the time $t_{end2}$ 510), and if the neurostimulator 106 was in a "therapy enabled" state at time $t_{start}$ 502, then the beeps 528 will be generated for the entirety of the magnet toggle interval 504 (from the time $t_{start}$ 502 to the time $t_{end1}$ 506), the long, low tone 526 will be generated during the time period 509 (between the magnet toggle interval endpoint time $t_{end1}$ 506 through the magnet force off interval endpoint time $t_{end2}$ 510), and then the long, low tone 526 will be generated again (or just continue to be generated) as soon as the magnetic field has been detected long enough to force the neurostimulator 106 into the "therapy disabled" state. When the neurostimulator 106 ceases to detect the magnetic field (at or after time $t_{forceoff}$ 514C in FIG. 6), neither the long, low tone 526 nor the beeps 528 are generated.

Alternatively or additionally, in some embodiments, the magnet tracking system 216 may cause different sounds to be produced whenever the magnet sensor 130 detects the presence of a magnet where one sound corresponds to the magnet toggle interval 504, another corresponds to the magnet force off interval 508 (and persists for some predetermined time after the endpoint $t_{end2}$ 510 when the magnet force off interval 508 has been exceeded, and still another corresponds to the time period 509 when the neurostimulator 106 is between the endpoint $t_{end1}$ 506 of the magnet toggle interval 504 and the endpoint $t_{end2}$ 510 of the magnet force off interval 508.

The sounds(s) may be generated by the neurostimulator 106 itself, e.g., using an annunciator element and/or circuit provided in the neurostimulator 106. Alternatively, the tone(s) may be generated by some other component of a neurostimulation system based on commands received from the implant. In other embodiments, rather than being auditory, the feedback may manifest in some other somatosensory effect, such as a vibration.

In still other embodiments, when the feedback is auditory, different tones may be used to indicate when the magnet has been recognized by the neurostimulator 106, when the neurostimulator 106 is in the time period 509 when it is susceptible of being toggled from a "therapy disabled" state to a "therapy enabled" state (or vice versa, as the case may be), and when the neurostimulator 106 has been forced to a "therapy disabled" state, i.e., after the endpoint of the magnet force off interval 508 at time $t_{end2}$ 510 has been reached or exceeded. For example, beeps generated at different frequencies may be used for the different auditory feedback signals. The patient (or caregiver) may hear: (1) a rapid series of beeps when the neurostimulator 106 is in the time period 509 (i.e., when it is susceptible of toggling between the "therapy enabled" and "therapy disabled" states); (2) a single short confirmatory beep when the neurostimulator 106 first detects the presence of the magnet (at time $t_{start}$ 502 in FIG. 6; and (3) a longer confirmatory tone for a few seconds once the magnet force off interval 508 has been exceeded (i.e., after time $t_{end2}$ 510 in FIG. 6) and the neurostimulator 106 thus has been forced into a "therapy disabled" state. In other embodiments, a distinct tone may also be generated if the presence of the magnet ceases to be detected by the neurostimulator 106 while the neurostimulator 106 is in the time period 509. In other words, if the neurostimulator 106 toggles states in the time period 509, a tone may be generated to confirm that such toggling occurred.

In still further embodiments, the tones selected may correspond to which state the neurostimulator 106 is in for so long as the neurostimulator 106 detects the presence of the magnet and for some predetermined time after the magnetic field is removed. For example, one tone may be associated with a "therapy enabled" state and another with a "therapy disabled" state. When the neurostimulator 106 has been forced into the "therapy disabled" state by leaving the magnet in place over the implant for at least as long as the magnet force off interval 508, the tone associated with the "therapy disabled" state may be generated for a few seconds after that interval has been exceeded to confirm that therapy indeed has been disabled and it is all right for the patient to remove the magnet. Other possibilities for the auditory feedback will be readily apparent.

It should be appreciated that while various embodiments have thus been described herein with regard to an neurostimulator 106, embodiments may be integrated within all sorts of active medical implantable devices, including but not limited to the following: implantable medical devices delivering treatment in the form of drug delivery, optical energy, and mechanical energy; implantable medical devices that may be controlled with means such as mechanical pressure or electrical fields and implantable medical devices capable of operating in more than one mode or with more than one setting, including both simple "on" and "off" modes and more complex cases in which modes correspond to various stimulation setting or types of therapy delivery.

Figure 7:
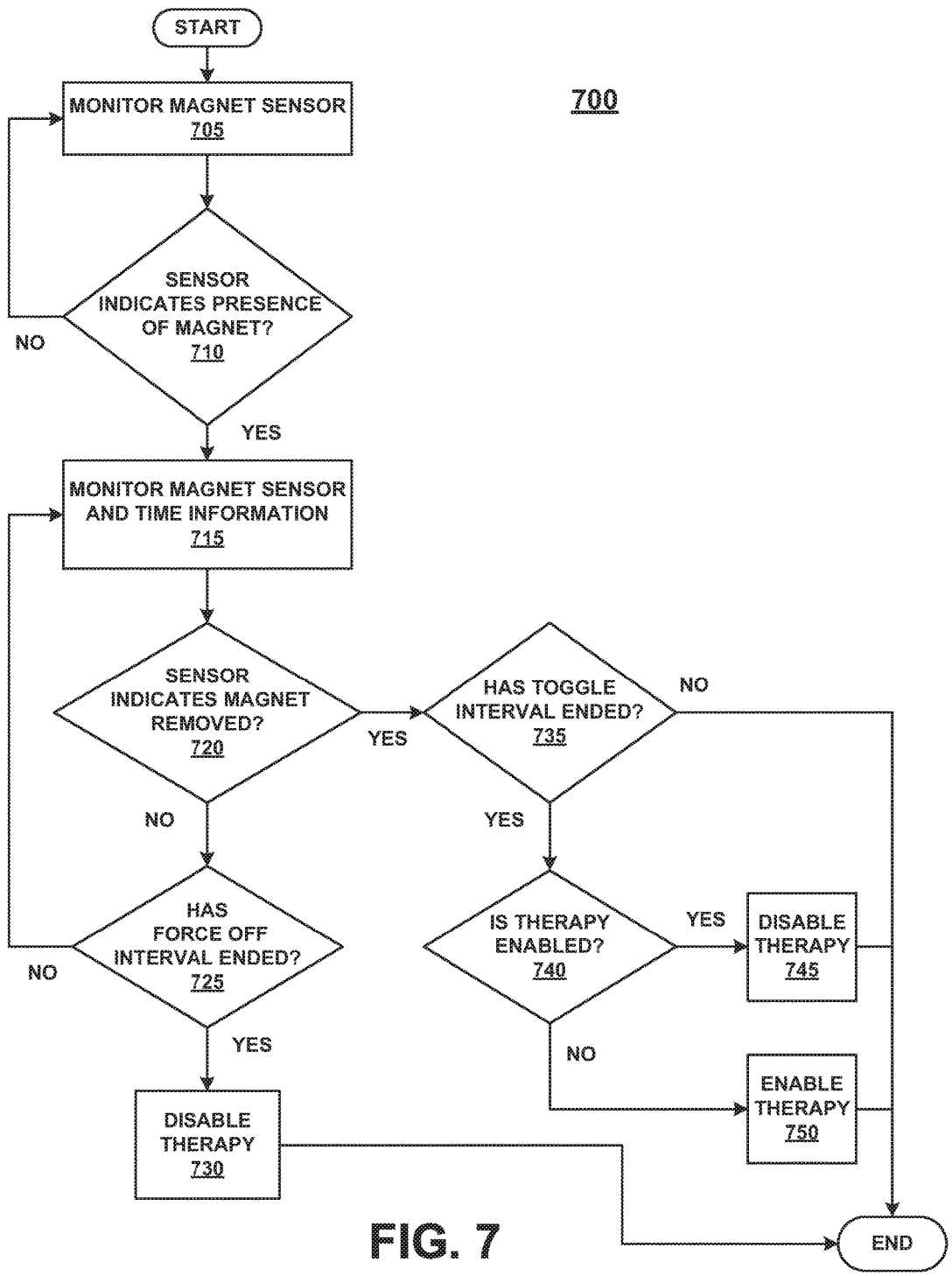
FIG. 7 is a flow chart of a method for selecting either a "therapy disabled" state or a "therapy enabled" state of an active implantable medical device, according to embodiments.

FIG. 7 is a flow diagram of elements of a method 700 for selecting a state of a neurostimulator 106, in accordance with an embodiment. The two states are "therapy enabled" and "therapy disabled." It will be appreciated that in other embodiments, the states of the neurostimulator 106 affected by use of the magnet may be different, such as simple "on" and "off" states, "on" and "standby" states, "sensing only" and "sensing and stimulation" states, and so on and so forth.

With reference now to FIG. 4 and FIG. 7, a neurostimulator 106 according to embodiments includes a communication subsystem 208 which enables communication between the neurostimulator 106, when implanted in a patient, and the outside world. The communication system 208 includes a magnet sensor 130 (for example, provided on a printed circuit board within a neurostimulator housing or otherwise associated with a control module 108 of a neurostimulator 106). The magnet sensor 130 generates an output signal when the magnet sensor 130 detects the presence of a magnetic field, such as from a magnet 220 that is provided to the patient. The magnet sensor output is processed and used by a magnet tracking subsystem 216 to determine whether and if so how to change the behavior of the neurostimulator 106 based on the presence of the magnet.

In FIG. 7 at block 705, the method and system monitors to determine whether the presence of a magnet is detected. This may be accomplished, for example, by monitoring the output of the magnet sensor 130. When at block 710 the neurostimulator 106 detects a magnet (e.g., at time $t_{start}$ 502 in FIG. 5), then at block 715 the magnet tracking subsystem 216 begins to track what happens next in terms of how long the presence of the magnet continues to be detected and whether the magnet ceases to be detected.

If at block 720 the neurostimulator 106 still detects a magnet, then at block 725 the neurostimulator 106 determines whether the magnet force off interval 508 has been exceeded. If the magnet force off interval 508 has been exceeded, then at block 730 the neurostimulator 106 is forced from a "therapy enabled" state into a "therapy disabled" state (if the neurostimulator 106 was in a "therapy enabled" state when the presence of the magnet was first detected at block 710) or it is left in a "therapy disabled" state (if it was in a "therapy disabled" state when the presence of the magnet was first detected at block 710).

If at block 720 the neurostimulator 106 no longer detects a magnet, then at block 735 the neurostimulator 106 determines whether the magnet toggle interval 504 has been exceeded. If the magnet toggle interval 504 has been exceeded (or has ended), then at block 740 the neurostimulator 106 determines which state the neurostimulator 106 is in. If the neurostimulator 106 is in a "therapy enabled" state at block 740, then at block 745, the neurostimulator 106 is transitioned (or toggled) to a "therapy disabled" state; if the neurostimulator 106 is in a "therapy disabled" state at block 740, then at block 750, the neurostimulator 106 is transitioned (or toggled) to a "therapy enabled" state. On the other hand, if at block 720 the neurostimulator 106 no longer detects a magnet and at block 735 the magnet toggle interval 504 has not been exceeded (or has not ended), then the neurostimulator 106 does nothing: That is, if the neurostimulator 106 was in a "therapy disabled" state just before the presence of the magnet was first detected at block 710 and the endpoint of the magnet toggle interval 504 is not reached before the magnet is no longer detected (e.g., the magnet is taken away from the implant site), then the neurostimulator 106 remains in the "therapy disabled" state. If the neurostimulator 106 was in a "therapy enabled" state just before the presence of the magnet was first detected at block 710, then the neurostimulator 106 remains in the "therapy enabled" state when the neurostimulator 106 ceases to detect the presence of the magnet before the magnet toggle interval is up.

Thus, if a patient or a patient's caregiver wants to ensure that an implanted neurostimulator 106 is in a state in which it is not able to deliver therapy (e.g., electrical stimulation), the patient or caregiver can accomplish this simply by applying the magnet for at least as long as the magnet force off interval 508. Once the patient is assured that the implant is in a "therapy disabled" state, the neurostimulator 106 can be returned to a "therapy enabled" state by removing the magnet from the neurostimulator 106 for a moment, then reapplying the magnet so that the clock associated with time $t_{start}$ 502 is reset, and the magnet tracking subsystem 216 again begins to track what happens next in terms of how long the presence of the magnet continues to be detected and whether the magnet ceases to be detected. The patient then can take the magnet away when the neurostimulator 106 is in the time period 509 when it is susceptible of toggling back to the "therapy enabled" state, which will cause the neurostimulator 106 to transition into the "therapy enabled" state. The patient (or caregiver) then can expect that the neurostimulator 106 will remain in the "therapy enabled" state unless and until the magnet sensor detects a magnet again. (Although in some circumstances the neurostimulator 106 may be configured to turn itself off under certain conditions that are not related to the presence or absence of a magnetic field.)

In some embodiments, the behavior of the neurostimulator 106 after it has been forced into a "therapy disabled" state may be more complex than in the example above. A method and system according to embodiments may require that, if the patient or caregiver wishes to transition the neurostimulator 106 to a "therapy enabled" state once a magnet has caused it to be forced into a "therapy disabled" state, the therapy will have to increase gradually up to a programmed therapeutic level rather than instantly be delivered at the therapeutic level when the neurostimulator 106 is toggled into a "therapy enabled" state by removing the magnet during the time period 509.

Similarly, embodiments are contemplated in which transitioning out of a "therapy enabled" state into a "therapy disabled" state is not a simple "on" to "off" action, but rather the therapy is gradually decreased over some predetermined period of time until it is considered to be completely disabled. Gradually, ramping a therapy up or down when the neurostimulator 106 transitions between states may be more appropriate in some applications of a neurostimulator 106 than in others. For example, if the patient is likely to sense the stimulation while it is being delivered then titrating a parameter (e.g., amplitude of the stimulation) up or down during state changes may be desirable. In other circumstances, abrupt changes in therapy may have unwanted results relative to the symptoms the therapy is intended to alleviate (e.g., the symptom of tremor for a movement disorders application of a neurostimulator).

In some embodiments, and as explained with reference to FIG. 6, above, the neurostimulator 106 causes one or more audible signals to be generated whenever the magnet is detected, wherever the neurostimulator 106 is in the time period 509 (i.e., susceptible of toggling between states); and whenever the magnet has been applied long enough to force the neurostimulator 106 into the "therapy disabled" state. In still other embodiments, whenever the magnet sensor 130 of the neurostimulator 106 detects the presence of the magnet, the neurostimulator 106 will generate a signal such as an audible signal that allows the patient or caregiver to gauge whether the magnet 220 is close enough to the magnet sensor 130. For example, a series of beeps at a certain tone may be configured to increase in frequency when the patient has the magnet 220 over a "sweet spot" relative to the magnet sensor 130 in the implanted neurostimulator 106, so that the patient can be assured that his or her use of the magnet will cause the behavior of the neurostimulator 106 the patient expects the magnet to cause.

It will be appreciated that there are numerous ways in which the method and system according to embodiments described above may be implemented. For example, software, hardware (including ASICs, FPGAs, and other custom electronics), and various combinations of software and hardware are all solutions that would be possible to practitioners of ordinary skill in the art of electronics and systems design. It should further be noted that the steps described herein as performed in software need not be, as some of them can be implemented in hardware, if desired, to further reduce computational load on the processor. In various embodiments, the methods and systems described above is implemented by processors and electrical components under the control of computer readable and computer executable instructions. The computer readable and computer executable instructions reside, for example, in a non-transitory data storage medium such as computer usable volatile and non-volatile memory. However, the computer readable and computer executable instructions may reside in any type of non-transitory computer readable storage medium.

It will also be appreciated that there are numerous possibilities for accomplishing the functions described above in a method and system according to embodiments. For example, the magnet tracking subsystem 216 (see the block diagram of FIG. 4) may be implemented as a magnet tracking software object capable of passing (via an interface such as an event messaging buffer) messages and information to other software objects, such as software objects that control delivery of therapy. The magnet tracking software object is configured to exist in one of a set of software object states, where each software object state is characterized by one or more of: the activity of the software object while in that software object state; the events or conditions that cause a transition of the software object into a different software object state; and the activities of the software object that occur when the software object transitions into a different software object state.

For example, the magnet tracking software object could be configured to be in a software object state labeled MAGNET_TRACKING_IDLE when a magnetic field is not currently detected by the neurostimulator 106. Upon initial detection of a magnetic field, the magnet tracking software object would enter a second software object state labeled MAGNET_TOGGLE_INTERVAL. At this transition, a timer implemented in software or hardware would be configured to run for the duration of the magnet toggle interval 504.

While in the MAGNET_TOGGLE_INTERVAL software object state, the magnet tracking software object would respond to several conditions. If a magnetic field becomes no longer detected, then the magnet tracking software object would re-enter the MAGNET_TRACKING_IDLE software object state and cancel the timer related to the magnet toggle interval 504. On the other hand, if this timer expires while still in MAGNET_TOGGLE_INTERVAL, the magnet tracking software object would enter a third software object state labeled MAGNET_FORCE_OFF_INTERVAL. At this transition, a timer implemented in software or hardware would be configured to run for the duration of the magnet force off interval 508.

While in the MAGNET_FORCE_OFF_INTERVAL software object state, the magnet tracking software object would respond to several conditions. If a magnetic field becomes no longer detected, then the magnet tracking software object would toggle therapy, e.g. from a "therapy disabled" state to a "therapy enabled" state or from a "therapy enabled" state to a "therapy disabled" state, would re-enter the MAGNET_TRACKING_IDLE software object state, and would cancel the timer related to the magnet force off interval 508. On the other hand, if this timer expires while still in MAGNET_FORCE_OFF_INTERVAL, the magnet tracking software object would set the neurostimulator state to a "therapy disabled" state and would enter a fourth software object state labeled MAGNET_HAS_BEEN_FORCED_OFF. The magnet tracking software object would remain in this state until a magnetic field becomes no longer detected, at which point it would return to the MAGNET_TRACKING_IDLE software object state.

Embodiments of methods and systems for controlling the state of a neurostimulator based on the presence or absence of a magnetic field (such as provided by an external magnet provided to the patient) thus have been described. While the present technology has been described in particular examples, it should be appreciated that the embodiments should not be construed as limited by such examples, but rather construed according to the claims.

Various example embodiments are thus described. All statements herein reciting principles, aspects, and embodiments of the present technology as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope, therefore, is not intended to be limited to the embodiments shown and described herein but rather is defined by the appended claims.

What is claimed is:

1. An active implantable medical device comprising:
    a sensor for detecting a presence of a magnetic field;
    a timer configured to keep track of the amount of time the sensor detects the magnetic field uninterrupted;
    a magnet tracking subsystem including a magnet tracking software object configured to exist in one of a plurality of software object states, and to transition to and from software object states based on one or more of a detection of a magnetic field, a duration of a detection of a magnetic field, and a state of the timer; and
    an interface for passing messages and information from the magnet tracking software object to at least one other software object that controls the state of the active implantable medical device, which state is one of a plurality of states comprising a first medical device activity state or a second, different medical device activity state,
    wherein the magnet tracking subsystem is configured to:
        monitor a number of times the state of the active implantable medical device has transitioned from a designated one of the plurality of states to another one of the plurality of states within a period of time, and
        prevent the state of the active implantable medical device from transitioning from the designated one of the plurality of states to the other one of the plurality of states when the number of times exceeds a threshold value.

2. The device of claim 1, wherein the plurality of software object states comprises:
    a first software object state corresponding to a condition when no magnetic field is detected by the sensor;
    a second software object state corresponding to the condition when a magnetic field has begun to be detected by the sensor and the timer has been initiated;
    a third software object state corresponding to the condition when a magnetic field has been detected by the sensor for longer than a first interval; and
    a fourth software object state corresponding to the condition when a magnetic field has been detected by the sensor for longer than both a first interval and a second interval.

3. The device of claim 2, wherein, the magnet tracking subsystem is configured to respond to a condition when a magnetic field ceases to be detected within the first interval by stopping the timer.

4. The device of claim 2, wherein the magnet tracking subsystem is configured to stop the timer upon a transition from the second software object state to the first software object state.

5. The device of claim 2, wherein the magnet tracking subsystem is configured to respond to a condition when a magnetic field is detected for the duration of the first interval by transitioning from the second software object state to the third software object state.

6. The device of claim 2, wherein the magnet tracking subsystem is configured to respond to a condition when a magnetic field ceases to be detected within the second interval by toggling the state of the active implantable medical device from the first medical device activity state to the second, different medical device activity.

7. The device of claim 2, wherein the magnet tracking subsystem is configured to toggle the state of the active implantable medical device from the first medical device activity state to the second, different medical device activity state upon a transition from the third software object state to the first software object state.

8. The device of claim 2, wherein, the magnet tracking subsystem is configured to respond to a condition when a magnetic field is detected throughout the entirety of the second interval by setting the state of the active implantable medical device to the designated one of the plurality of states.

9. The device of claim 2, wherein, the magnet tracking subsystem is configured to set the state of the active implantable medical device to the designated one of the plurality of states upon a transition from the third software object state to the fourth software object state.

10. The device of claim 2 wherein the magnet tracking subsystem is configured to respond to the condition when the second interval has been exceeded by ensuring that the active implantable medical device is in a predetermined one of the first medical device activity state or the second medical device activity state.

11. The device of claim 2, wherein the magnet tracking subsystem is configured to ensure that the active implantable medical device is in a predetermined one of the first medical device activity state or the second medical device activity state upon a transition from the third software object state to the fourth software object state.

12. The device of claim 2, further comprising:
    a feedback signal generator, the feedback signal generator configured to generate:
        a first audible tone whenever the magnet tracking subsystem is in the second software object state;
        a second, different audible tone whenever the active implantable medical device is susceptible of transitioning from the first medical device activity state to the second medical device activity state between the end of the first interval and the end of the second interval; and
        whichever of the first or second audible tones that corresponds to a predetermined one of the first or second medical device activity states if the sensor still detects the presence of the magnetic field after the second interval.

13. The device of claim 1, wherein:
    the first medical device activity state corresponds to a state in which a therapy the active implantable medical device is configured to deliver is disabled, and
    the second medical device activity state corresponds to a state in which a therapy the active implantable medical device is configured to deliver is enabled.

14. The device of claim 2, further comprising:
    a feedback signal generator, the feedback signal generator configured to generate:
        a first audible tone when the magnet tracking subsystem is in the second software object state;

a second, different audible tone when the magnet tracking subsystem is in the third software object state; and a third, different audible tome when the magnet tracking subsystem is in the fourth software object state.

15. An active implantable medical device comprising:

a sensor for detecting a presence of a magnetic field;

a timer configured to keep track of the amount of time the sensor detects the magnetic field uninterrupted;

a magnet tracking subsystem including a magnet tracking software object configured to exist in one of a plurality of software object states, and to transition to and from software object states based on one or more of a detection of a magnetic field, a duration of a detection of a magnetic field, and a state of the timer; and an interface for passing messages and information from the magnet tracking software object to at least one other software object that controls the state of the active implantable medical device, which state is one of a therapy enabled state or a therapy disabled state, wherein the plurality of software object states comprises a first software object state corresponding to a condition when no magnetic field is detected by the sensor, a second software object state corresponding to the condition when a magnetic field has begun to be detected by the sensor and the timer has been initiated, a third software object state corresponding to the condition when a magnetic field has been detected by the sensor for longer than a first interval, and a fourth software object state corresponding to the condition when a magnetic field has been detected by the sensor for longer than both a first interval and a second interval wherein the magnet tracking subsystem is configured to:

set the state of the active implantable medical device to the therapy disabled state upon a transition from the third software object state to the fourth software object state;

monitor a number of times there has been a transition from the third software object state to the fourth software object state within a period of time, and prevent the state of the active implantable medical device from being changed from the therapy disabled state to the therapy enabled state when there is a transition from the third software object state to the first software object state, and the number of times exceeds a threshold value.

* * * * *